United States Patent
Nolte

(10) Patent No.: US 8,595,608 B2
(45) Date of Patent: Nov. 26, 2013

(54) METHOD FOR TRANSFERRING A NUMBER OF MEDICAL IMAGE DATA RECORDS AND SYSTEM FOR MANAGING IMAGE DATA RECORDS

(75) Inventor: Björn Nolte, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 383 days.

(21) Appl. No.: 13/012,944

(22) Filed: Jan. 25, 2011

(65) Prior Publication Data

US 2011/0214041 A1  Sep. 1, 2011

(30) Foreign Application Priority Data

Feb. 26, 2010 (DE) .......................... 10 2010 009 460

(51) Int. Cl.
G06F 7/02 (2006.01)
H03M 13/00 (2006.01)

(52) U.S. Cl.
USPC .......................................................... 714/819

(58) Field of Classification Search
USPC ........... 714/48, 746, 748, 750, 807, 755, 758, 714/799, 819; 705/2–3; 600/407
See application file for complete search history.

(56) References Cited

U.S. PATENT DOCUMENTS

| | | | |
|---|---|---|---|
| 5,291,399 A * | 3/1994 | Chaco | 705/3 |
| 5,822,544 A * | 10/1998 | Chaco et al. | 705/2 |
| 7,783,072 B2 * | 8/2010 | Work et al. | 382/100 |
| 8,140,350 B2 * | 3/2012 | Rothpearl et al. | 705/2 |
| 8,156,440 B2 * | 4/2012 | Amon | 715/748 |
| 2006/0173246 A1 * | 8/2006 | Zaleski | 600/300 |

OTHER PUBLICATIONS

Lo et al., Interactive and adaptive progressive transmission of medical images, 2007, IEEE, p. 5669-5672.*
Zain et al., Evaluation of medical image watermarking with tamper detection and recovery (AW-TDR), Aug. 2007, IEEE, p. 5661-5664.*
M. Schneider et al.: "A Robust Content Based Digital Signature for Image Authentication", IEEE Proceedings, Int. Conf. on Image Proc. IEEE, 1996, p. 227-230; Others; 1996.
Schütze et al.: "Ein Lösungsweg, um medizinische Bilder mit digitalen Signaturen nach dem DICOM-Standard zu versehen: Embedded Systems", Fortschr. Röntgenstr. 2005, ISSN: 1438-9029, Georg Thieme Verlag, Stuttgart, 2005, p. 124-129; Others; 2005.

* cited by examiner

*Primary Examiner* — Shelly A Chase
(74) *Attorney, Agent, or Firm* — Harness, Dickey & Pierce, P.L.C.

(57) ABSTRACT

A method is disclosed for transferring a number of medical image data records from a first computation facility to a second computation facility, with the second computation facility sending a transmission confirmation to the first computation facility after transmission is completed. In at least one embodiment, before the image data records are transmitted, a first checksum is determined for all the image data records and sent with the image data records; the first checksum is extracted at the second computation facility and is compared with a second checksum determined from the transmitted image data records in the same manner as the first checksum; and the transmission confirmation indicates a failure if the checksums do not correspond.

12 Claims, 2 Drawing Sheets

METHOD FOR TRANSFERRING A NUMBER OF MEDICAL IMAGE DATA RECORDS AND SYSTEM FOR MANAGING IMAGE DATA RECORDS

PRIORITY STATEMENT

The present application hereby claims priority under 35 U.S.C. §119 on German patent application number DE 10 2010 009 460.9 filed Feb. 26, 2010, the entire contents of which are hereby incorporated herein by reference.

FIELD

At least one embodiment of the invention generally relates to a method for transferring a number of medical image data records from a first computation facility to a second computation facility, with the second computation facility sending a transmission confirmation to the first computation facility after transmission is completed, as well as an associated system for managing medical image data records.

BACKGROUND

As technology continues to develop, it is not only usual with medical image recording facilities to generate larger image data records with higher resolution but frequently as part of a patient examination a plurality of images are also frequently generated and stored as image data records. It is conceivable for example to record up to 3,000 images as part of a single examination, so that an enormous storage capacity is required. It is therefore usual to remove the images, in particular even immediately after recording, from the corresponding computation facility of the image recording facility and to transmit the image data records to a second computation facility, for example a central diagnostic workstation or even directly to a computation facility of an image management system (PACS archive computer).

Medical image data records are currently stored and further processed almost exclusively in what is known as the DICOM standard (digital imaging and communication in medicine). It can of course generally come about that transmission failures occur or the received image data records cannot be stored by the second computation facility and/or inserted into the archive. For such problems the DICOM standard provides a storage commitment function, with which the sending, in other words the first, computation facility can enquire, after the data transmission has been confirmed, whether the transferred data has been safely stored. This is of interest for example when, as described above for example, the first computation facility wishes to delete the image data records and would like to ensure that they have also been archived or safely transmitted. When the second computation facility receives such a storage commitment request, it checks whether the received image data records have been safely stored and, if so, sends a corresponding confirmation back to the first computation facility.

However this storage commitment service in the DICOM standard is only rarely used, as on the other hand the intention is to achieve a high-performance transfer of large quantities of data and such additional messages are prejudicial to this. It is therefore currently frequently the case that only an early transmission confirmation is sent directly after receipt of the image data records, from which it cannot however be determined whether all the images were transmitted correctly or whether the archiving or storage of the images was successful. In the worst instance it may therefore be that if the first computation facility has already deleted the image data records, recordings are lost completely.

SUMMARY

In at least one embodiment of the invention, a method is specified for transferring medical image data records, wherein it can be ascertained without transmitting additional messages and in particular without modifying or slowing down transmission whether the image data records have been transmitted correctly.

In at least one embodiment, provision is made before the image data records are transmitted for a first checksum to be determined for all the image data records and to be sent with the image data records, with the first checksum being extracted at the second computation facility and being compared with a second checksum determined from the transmitted image data records in the same manner as the first checksum and the transmission confirmation indicating a failure if the checksums do not correspond.

A single checksum is therefore created for all the image data records, to make it possible to confirm failure-free transmission in the most compact manner possible. It is also particularly advantageous if the checksum is sent with the image data records themselves, in other words no modifications advantageously have to be made to the actual transmission mechanisms. In a particularly expedient embodiment provision can be specifically be made here for image data records in the DICOM format to be used and the first checksum to be sent as private content of an image data record, in particular of the last image data record. This ultimately means that only one image data record is supplemented by a self-defined metadata item, specifically the checksum of all the image data records to be transmitted. If the checksum is contained in this manner in one of the image data records themselves, there is no need to modify the further transmission mechanisms in any way; processing operations for sending or receiving the image data records can remain exactly the same, so that at least one embodiment of the inventive method can be realized in a simple manner.

When the image data records are received at the second computation facility, the first checksum is again extracted and a checksum, specifically the second checksum, is again created for all the image data records, naturally using the same checksum algorithm. It should be pointed out here that ultimately all the standard checksum algorithms can be used in the context of at least one embodiment of the inventive method, for example an md5sum algorithm. The first and second checksums can now be compared and indicate whether the image data records have been safely transferred.

It is thus possible in a simple manner to check the safe transmission of image data records. No modifications have to be made to the actual transmission mechanism and the transmission of further messages is also not necessary. This is achieved by determining the checksum on both sides, transferring the first checksum and carrying out the comparison on the receive side, so that the feedback can be integrated in the transmission confirmation in a simple manner.

In a further embodiment of the inventive method provision can be made for the image data records to be processed for send and/or receive purposes by a pipeline having at least one filter, the determination of the checksum and/or the comparison of the checksums forming such a filter. Such pipelines are generally known and contain for example a first filter which reads out data from the storage facility of the computation facility and a filter which starts the actual transmission of data to the second computation facility. Correspondingly present on the receive side are a filter which receives the data and a filter which can ultimately store the data on a storage facility there. Further filters can be provided between these respective filters, for example for processing the data for the purposes of a compression or decoding and decompression or decoding respectively. At least one embodiment of the inventive method can now be realized simply by adding a further filter on the sending side for determining the checksum and inserting it into the data stream to be transmitted and conversely providing a filter for extracting the checksum and determining the second checksum and for the comparison on the receive side.

In a particularly advantageous embodiment, provision can be made here for the image data records to be compressed and/or encoded in the first computation facility after determination of the first checksum and for the determination of the second checksum to take place after decompression and/or decoding. For example, if we look at the above-mentioned pipelines, provision can be made for determination of the first checksum immediately after the filter for reading in from the storage facility, while extraction of the first checksum and calculation of the second checksum take place on the receive side immediately before the image data records are stored on the storage facility of the second computation facility there. This means that not only is the safe transmission of the image data records checked but at the same time it is ascertained if failures have occurred in the processing mechanisms, in other words in particular during compression and/or encoding. This further enhances safe operation.

Provision can also be made for a transmission confirmation according to the DICOM standard to be used, in particular a transmission confirmation comprising a failure flag. A DICOM association response for example can be used as the transmission confirmation, which in any case contains a failure flag, which is set when it has been ascertained that the first checksum and the second checksum do not correspond. In this way the method assists simple realization in that the type of back confirmation ultimately does not have to be modified.

As already mentioned, at least one embodiment of the inventive method can be employed particularly advantageously when a computation facility of an image recording facility is used as the first computation facility and/or a computation facility at a diagnostic workstation or a computation facility of an image management system is used as the second computation facility. There is generally only limited storage space available specifically with the computation facilities of image recording facilities, so that the storage space should be emptied again as quickly as possible by deleting the recorded image data records. However this requires the recorded image data records to be transmitted to a second computation facility, for example a computation facility at a diagnostic workstation, at which for example images from different image recording facilities and/or modalities are collected for diagnosis, or they have to be transmitted to a computation facility of an image management system (PACS). It is possible to ensure with the inventive method that deletion only takes place at the image recording facility when the data has been transmitted safely and in its entirety.

As well as the method, at least one embodiment of the present invention also relates to a system for managing medical image data records, comprising at least two computation facilities and configured to implement the inventive method. It can be a hospital network for example, in which computation facilities of different image recording facilities, different workstation computers and an archive computer of the image management system are connected to one another. Whenever image data records have to be transmitted within this system from a first computation facility to a second computation facility, at least one embodiment of the inventive method can be employed to obtain confirmation immediately after transmission whether the image data records have been transmitted without failure. The image recording facilities here can comprise for example CT facilities, MR facilities, X-ray facilities and/or ultrasound image recording facilities.

All the statements relating to at least one embodiment of the inventive method can be applied in a similar manner to at least one embodiment of the inventive system.

BRIEF DESCRIPTION OF THE DRAWINGS

Further advantages and details of the present invention will emerge from the example embodiments set out in the following and with reference to the drawings, in which.

DETAILED DESCRIPTION OF THE EXAMPLE EMBODIMENTS

Figure 1:
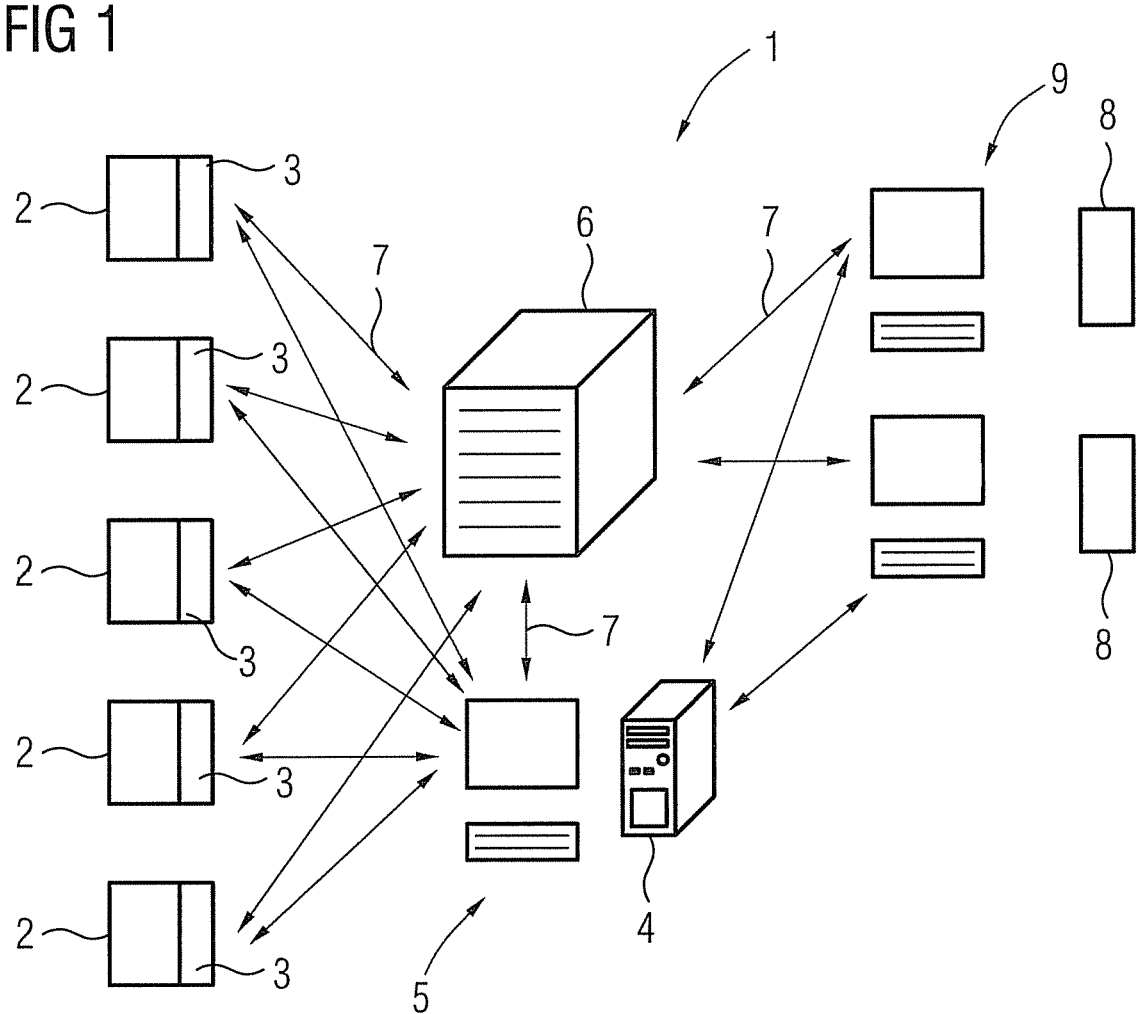
FIG. 1 shows an embodiment of an inventive system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an inventive image management system 1, as can be employed for example in a hospital. A number of image recording facilities 2 are provided, illustrated here only in an abstract manner and possibly comprising for example an MR facility, at least one CT facility, at least one ultrasound image recording facility, at least one X-ray facility and the like. Each of these image recording facilities features its own computation facility 3, in which recorded image data records can be buffered for example in a storage facility, such as a hard disk. An examination generally generates a plurality of image data records taking up a large storage volume.

Therefore provision is made in the image management system 1 for transmitting the image data records of an examination after completion of said examination to a further, second computation facility and therefore to delete them from the first computation facility 3 of the corresponding image recording facility 2.

The second computation facility in the example illustrated here can be a computation facility 4 of a diagnostic workstation 5 or even a computation facility 6 for the central archiving of the image data records in the image management system 1, for example a PACS server. Of course for a further transfer of the image data records the computation facility 4 can also form a first computation facility, when diagnosed image data records to be archived are to be transferred from the diagnostic workstation 5 to the computation facility 6, in other words the server, for final archiving.

Communication connections 7 can be set up between the different computation facilities 3, 4, 6, for example as part of a network such as an intranet, to transmit image data records. Computation facilities 8 at different further workstations 9 can also be connected to such a network.

The transmission of image data records takes place in the system 1 based on an embodiment of the inventive method. This means that first a checksum is calculated for all the image data records to be transmitted. This checksum is then transmitted to the second computation facility. It is extracted again there and a second checksum is determined from the received image data records, with the same checksum algorithm, here an md5sum algorithm, being used for this purpose. After a comparison of the two checksums, if the comparison fails, in other words if the transmission has clearly failed, the failure flag of the transmission confirmation to be sent is set so that when the transmission confirmation is received at the first computation facility it can be ascertained whether the transmission was successful. The transmission of the checksum with the image data records is realized in this exemplary embodiment in that it is integrated as private content in the last image data record, as the image data records are present in the DICOM format, in which such private content is permitted.

With an embodiment of the inventive method, major modification of the transmission mechanisms is therefore not required and a larger number of messages does not have to be exchanged between the first computation facility and the second computation facility.

Figure 2:
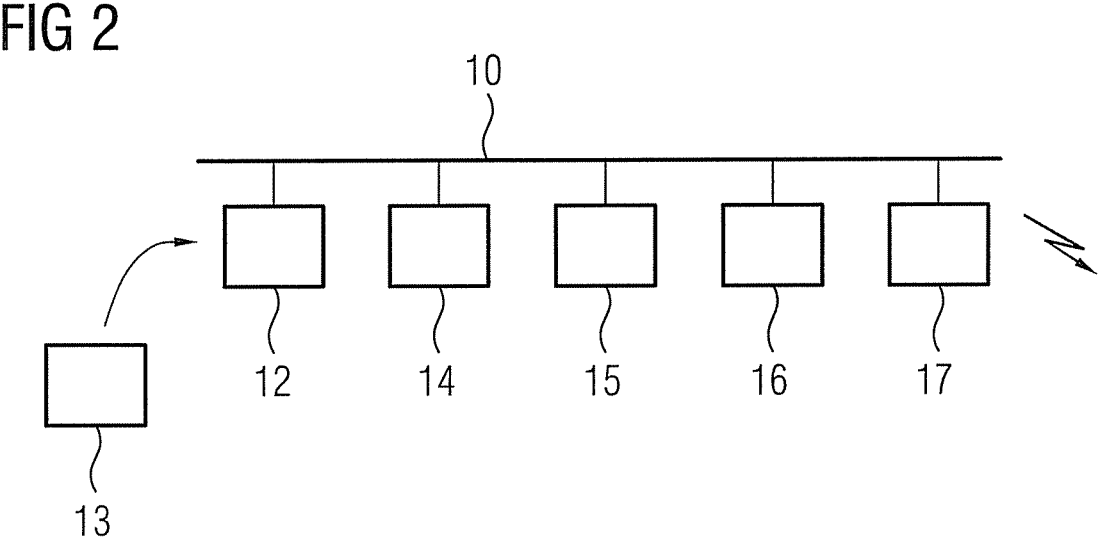
FIG. 2 shows a send pipeline.
Figure 3:
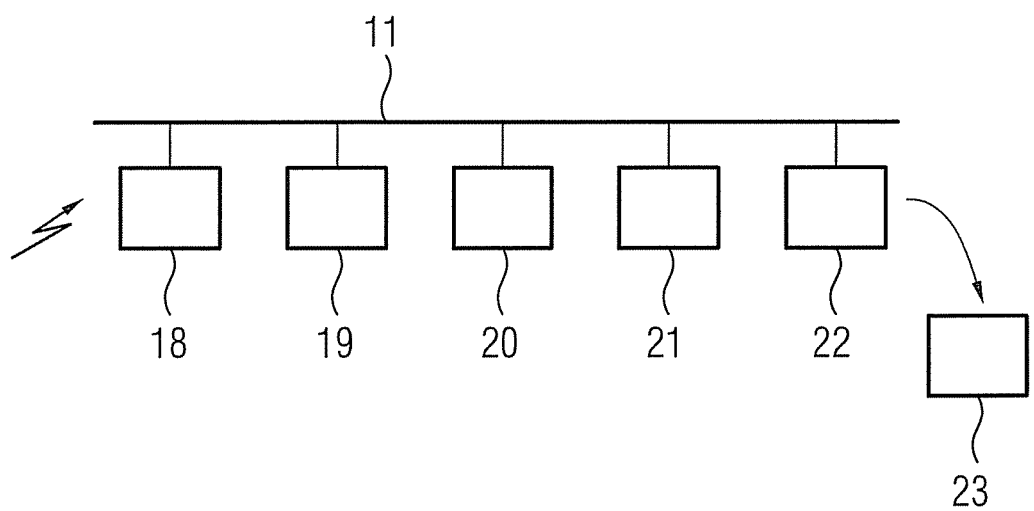
FIG. 3 shows a receive pipeline.

This is explained in more detail below with reference to FIGS. 2 and 3, FIG. 2 showing a send pipeline 10 and FIG. 3 showing a receive pipeline 11. The pipelines 10, 11 here comprise a number of filters, which represent processing steps in the send process for the image data records. These are generally also realized as individual software units.

If image data records are to be transmitted, they therefore pass first through the send pipeline 10 provided on the first computation facility, for example the computation facility 3 of an image recording facility 2. A first filter 12 reads the image data records from a storage facility 13 of the first computation facility, for example from a hard disk. Immediately after this is a filter 14, used to determine the first checksum. Also in the filter 14 this first checksum is added to the last image data record as private content. The filter 15 serves to compress the image data records while the filter 16 is used for encoding. Color codings 16 for example can be modified in such a filter 16, for example by means of an RGB->YBR filter. Naturally a number of compression and encoding filters 15, 16 can also be provided. The filter 17 finally sends the data of the image data records to a second computation facility in the network, for example the computation facility 6.

The data is received at the second computation facility by a first filter 18 of the receive pipeline 11. Decoding then takes place in a decoding filter 19. A decompression filter 20 unpacks the data. Only then is the first checksum extracted again from the image data records in a filter 21 and the second checksum is then calculated. The comparison of the checksums and the modification of the failure flag that is sometimes required also take place by means of the filter 21. The filter 22 finally serves to store the image data records on a storage facility 23 of the second computation facility. To implement the inventive method therefore only the filters 14 and 21 have to be integrated in the pipelines 10, 11. Further modifications are not necessary. Because the checksum calculation takes place before encoding and compression processes and after decoding and decompression processes respectively, not only is correct transmission checked but also correct processing in the context of the further filters of the pipelines 10, 11.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1 Image management system
2 Image recording facility
3 Computation facility
4 Computation facility
5 Diagnostic workstation
6 Computation facility
7 Communication connection
8 Computation facility
9 Workstation
10 Send pipeline
11 Receive pipeline
12 Filter
13 Storage facility
14 Filter
15 Filter
16 Filter
17 Filter
18 Filter
19 Decoding filter
20 Decompression filter
21 Filter
22 Filter
23 Storage facility

What is claimed is:

1. A method for transferring a number of medical image data records from a first computation facility to a second computation facility, the second computation facility sending a transmission confirmation to the first computation facility after transmission is completed, comprising:
   determining a first checksum, before the medical image data records are transmitted, for all the medical image data records, the determined first checksum being sent with the medical image data records;
   extracting the first checksum at the second computation facility; and
   comparing the first checksum with a second checksum determined from the transmitted medical image data records in the same manner as the first checksum, the transmission confirmation indicating a failure if the first and second checksums do not correspond.

2. The method as claimed in claim 1, wherein the medical image data records are in the DICOM format and wherein the first checksum is sent as private content of one of the medical image data records.

3. The method as claimed in claim 1, wherein the medical image data records are processed for at least one of send and receive purposes by a pipeline having at least one filter, at least one of the determination of the checksum and the comparison of the first and second checksums forming such a filter.

4. The method as claimed in claim 1, wherein the medical image data records are at least one of compressed and encoded in the first computation facility after determination of the first checksum and the determination of the second checksum takes place after at least one of decompression and decoding.

5. The method as claimed in claim 1, wherein a transmission confirmation according to the DICOM standard is used.

6. The method as claimed in claim 1, wherein a computation facility of an image recording facility is used as at least one of the first computation facility and a computation facility at a diagnostic workstation or a computation facility of an image management system is used as the second computation facility.

7. A system for managing medical image data records, comprising:
   at least two computation facilities, configured to
   determine a first checksum, before medical image data records are transmitted from a first of the at least two computation facilities to a second of the at least two computation facilities, the determined first checksum being sent with the medical image data records;
   extract the first checksum at the second computation facility; and
   compare the first checksum with a second checksum determined from the transmitted medical image data records in the same manner as the first checksum, a transmission confirmation indicating a failure if the first and second checksums do not correspond.

8. The method as claimed in claim 2, wherein the first checksum is sent as private content of a relatively last one of the number of medical image data records.

9. The method as claimed in claim 2, wherein the medical image data records are processed for at least one of send and receive purposes by a pipeline having at least one filter, at least one of the determination of the checksum and the comparison of the first and second checksums forming such a filter.

10. The method as claimed in claim 8, wherein the medical image data records are processed for at least one of send and receive purposes by a pipeline having at least one filter, at least one of the determination of the checksum and the comparison of the first and second checksums forming such a filter.

11. The method as claimed in claim 5, wherein the transmission confirmation comprises a failure flag.

12. A non-transitory computer readable medium including a computer program product, the computer program product comprising instructions, which when executed on a computer, causes the computer to perform functions including:
    determining a first checksum for all the medical image data records, before a medical image data records are transmitted from a first computation facility to a second computation facility, the determined first checksum being sent with the medical image data records;
    extracting the first checksum at the second computation facility; and
    comparing the first checksum with a second checksum determined from the transmitted medical image data records in the same manner as the first checksum, the second computation facility sending a transmission confirmation to the first computation facility after the transmission is completed, the transmission confirmation indicating a failure if the first and second checksums do not correspond.

* * * * *